(12) United States Patent
Sortwell et al.

(10) Patent No.: US 7,459,152 B2
(45) Date of Patent: Dec. 2, 2008

(54) ERYTHROPOIETIN ADMINISTRATION TO IMPROVE GRAFT SURVIVAL

(75) Inventors: Caryl E. Sortwell, Chicago, IL (US); Timothy J. Collier, Deerfield, IL (US)

(73) Assignee: Rush University Medical Center, Chicago, IL (US)

( * ) Notice: Subject to any disclaimer, the term of this patent is extended or adjusted under 35 U.S.C. 154(b) by 461 days.

(21) Appl. No.: 10/830,705

(22) Filed: Apr. 23, 2004

(65) Prior Publication Data

US 2004/0259071 A1 Dec. 23, 2004

Related U.S. Application Data

(60) Provisional application No. 60/464,771, filed on Apr. 23, 2003.

(51) Int. Cl.
*C12N 5/08* (2006.01)
(52) U.S. Cl. .................... 424/93.1; 424/93.7; 435/377; 435/365; 435/368
(58) Field of Classification Search ................. None
See application file for complete search history.

(56) References Cited

U.S. PATENT DOCUMENTS

| | | | |
|---|---|---|---|
| 4,703,008 A | 10/1987 | Lin | |
| 5,082,670 A | 1/1992 | Gage et al. | |
| 5,441,868 A | 8/1995 | Lin | |
| 5,512,661 A | 4/1996 | Shooter et al. | |
| 5,547,933 A | 8/1996 | Lin | |
| 5,612,211 A | 3/1997 | Wilson et al. | |
| 5,618,531 A | 4/1997 | Cherksey | |
| 5,618,698 A | 4/1997 | Lin | |
| 5,621,080 A | 4/1997 | Lin | |
| 5,650,148 A | 7/1997 | Gage et al. | |
| 5,650,298 A | 7/1997 | Bujard et al. | |
| 5,653,975 A | 8/1997 | Baetge et al. | |
| 5,656,481 A | 8/1997 | Baetge et al. | |
| 5,750,376 A | 5/1998 | Weiss et al. | |
| 5,753,506 A | 5/1998 | Johe | |
| 5,756,349 A | 5/1998 | Lin | |
| 5,773,569 A | 6/1998 | Wrighton et al. | |
| 5,798,113 A | 8/1998 | Dionne et al. | |
| 5,800,828 A | 9/1998 | Dionne et al. | |
| 5,830,851 A | 11/1998 | Wrighton et al. | |
| 5,856,298 A | 1/1999 | Strickland | |
| 5,888,772 A | 3/1999 | Okasinski et al. | |
| 5,955,422 A | 9/1999 | Lin | |
| 5,965,125 A | 10/1999 | Mineau-Hanschke | |
| 5,986,047 A | 11/1999 | Wrighton et al. | |
| 5,994,313 A | 11/1999 | Crabtree et al. | |
| 6,083,523 A | 7/2000 | Dionne et al. | |
| 6,165,783 A | 12/2000 | Weiss et al. | |
| 6,183,965 B1 | 2/2001 | Verdine et al. | |
| 6,254,865 B1 | 7/2001 | Freed et al. | |
| 6,271,436 B1 | 8/2001 | Piedrahita et al. | |
| 6,277,820 B1 | 8/2001 | Rosenthal et al. | |
| 6,284,539 B1 | 9/2001 | Bowen et al. | |
| 6,368,854 B2 | 4/2002 | Weiss et al. | |
| 6,369,294 B1 | 4/2002 | Piedrahita et al. | |
| 6,395,546 B1 | 5/2002 | Zobel et al. | |
| 6,419,920 B1 | 7/2002 | Mineau-Hanschke | |
| 6,444,205 B2 | 9/2002 | Dinsmore | |
| 6,451,306 B1 | 9/2002 | Tuszynski et al. | |
| 6,472,181 B1 | 10/2002 | Mineau-Hanschke | |
| 6,497,872 B1 | 12/2002 | Weiss et al. | |
| 6,610,540 B1 * | 8/2003 | Csete et al. | 435/375 |
| 6,638,501 B1 | 10/2003 | Bjornson et al. | |
| 2003/0103949 A1 * | 6/2003 | Carpenter et al. | 424/93.21 |
| 2004/0092444 A1 * | 5/2004 | Digicaylioglu et al. | 514/12 |

FOREIGN PATENT DOCUMENTS

| WO | WO 93/01275 | 1/1993 |
|---|---|---|
| WO | WO 94/02593 | 2/1994 |
| WO | WO 94/10292 | 5/1994 |
| WO | WO 94/25055 | 11/1994 |
| WO | WO 96/04368 | 2/1996 |
| WO | WO 97/44442 | 11/1997 |
| WO | WO 98/30678 | 7/1998 |

OTHER PUBLICATIONS

Drucker and Diaz, Cell Mol Neurobiol, Jun. 2004, 24(3):301-316.*
Maiese et. al., JAMA, Jan. 5, 2005, 293(1):90-95.*
Lindvall and Bjorklund, NeuroRX, Oct. 2004, 1(4):382-93.*
Schierle et. al.Nature Med, Jan. 1999, 5(1):97-100.*
Widner et. al., NEJM, Nov. 26, 1992, 327(22)1556-63.*

(Continued)

*Primary Examiner*—David S Romeo
*Assistant Examiner*—Daniel C Gamett
(74) *Attorney, Agent, or Firm*—Foley & Lardner LLP

(57) ABSTRACT

The present invention provides methods, compounds and kits for increasing the viability of cells. The methods involve treating cells that make up a tissue graft with erythropoietin before, during or after delivery or administration. The method can employ cells of different types, including cells of neural or paraneural origin, such as adrenal chromaffin cells. Also useful are cell lines grown in vitro. Cells not of neural or paraneural origin, such as fibroblasts, may also be used following genetic alteration to express a desired neural product such as a neurotransmitter or a neuronal growth factor. The method is used to treat neurological diseases such as Parkinson's disease, Alzheimer's disease, Huntington's disease, epilepsy, and traumatic brain or spinal cord injury.

5 Claims, 4 Drawing Sheets

OTHER PUBLICATIONS

Chong et. al., J Neurosci Res, Mar. 2003, 71(5):659-69.*
Ehrenreich et. al., Molecular Medicine, 2002, 8(8):495-505.*
Gorio et. al., Proc Natl Acad Sci U S A, Jul. 9, 2002, 99(14):9450-5.*
Genc et al., (2001), Neuroscience Letters 298:139-141.*
Verhoeyen and Cosset, (2004) Blood 103(9): 3248-3249.*
Brines et al., Proc Natl Acad Sci U S A. Sep. 12, 2000;97(19):10526-10531.*
Animal Care and Use,(Oct. 11, 2001), http://www.jhu.edu/animalcare/rat.htm, Accessed Oct. 3, 2007.*
Leksell and Jernberg, "Stereotaxis and Tomography," *Acta Neurochir*. 52:1-7, 1980. Published by Springer-Verlag.
"Neural Grafting in the Mammalian CNS," Bjorklun and Stenveni, eds.; Das, Ch. 3 pp. 23-30; Freed Ch. 4, pp. 31-40; Stenevi et al., Ch. 5, pp. 41-49; Brundin et al., Ch. 6, pp. 51-59; David et al., Ch. 7, pp. 61-69; and Seiger, Ch. 8, pp. 71-77, 1985. Published by Elsevier.
Burns et al., "A primate model of parkinsonism: Selective destruction of dopaminergic neurons in the pars compacta of the substantia nigra by N-methyl-4-phenyl-1,2,3,6-tetrahydropyridine," *Proc. Natl. Acad. Sci.* USA, 80:4546-4550, Jul. 1983.
Bankiewicz et al., Hemiparkinsonism in monkeys after unilateral internal carotid artery infusion of 1-methyl-4-phenyl-1,2,3,6-tetrahydropyridine (MPTP), *Life Sci.*, 39:7-16, 1986. Published by Pergamon Press.
Leksell et al., "A new fixation device for the Leksell stereotaxic system," *J. Neurosurg.* 66:626-629, 1987.
Duncan et al., "Transplantation of oligodendrocytes and Schwann cells into the spinal cord of the myelin-deficient rat," *J. Neurocytology*, 17:351-360, 1988. Published by Chapman and Hall, Ltd.
Burns et al., "The clinical syndrome of striatal dopamine deficiency," *N. Engl. J. Med.*, 312(22), 1418-1421, May 30, 1985. Published by the Massachusetts Medical Society.
Wolff et al., "Grafting fibroblasts genetically modified to produce L-dopa in a rat model of Parkinson disease," *Proc. Natl. Acad. Sci USA*, 86:9011-9014, Nov. 1989.
Neural Grafting: Repairing the Brain and Spinal cord, Chapter 4: "General Features of Neural Grafting," pp. 39-57; Pub. by Congress of the U.S., Office of Technology and Assessment, Washington, DC, Oct. 1990.
Sagen, et al., "Monoaminergic Neural Transplants Prevent Learned Helplessness in a Rat Depression Model," *Biol Psychiatry*, 28(12), pp. 1037-1048, 1990. Published by the Society of Biological Psychiatry.
Bankiewicz et al., "The effect of fetal mesencephalon implants on primate MPTP-induced parkinsonism," *J. Neurosurg.*, 72:231-244, Feb. 1990.
Taylor et al., "Improvements in MPTP-induced object retrieval deficits and behavioral deficits after fetal nigral grafting in monkeys," *Prog. Brain Res.*, 82:543-559, 1990. Published by Elsevier.
Bjorklund et al., "Reconstruction of the nigrostriatal dopamine pathway by intracerebral nigral transplants," *Brain Res.*, 177:555-560, 1979. Published by Elsevier.
Lindvall et al., "Grafts of fetal dopamine neurons survive and improve motor function in Parkinson's disease," *Science*, 247:574-577, Feb. 2, 1990.
Freed, "Substantia nigra grats and Parkinson's disease: from animal experiments to human therapeutic trials," Restor. Neurol. Neurosci., 3:109-134 (1991).
Fisher et al., "Survival and function of intrastriatally grafted primary fibroblasts genetically modified to produce L-dopa," Neuron, 6:371-380, Mar. 1991.
Gage and Fisher, "Intracerebral Grafting: A tool for the Neurobiologist," *Neuron*, 6:1-12, Jan. 1991. Published by Cell Press.
Lindvall et al., "Human fetal dopamine neurons grafted into the striatum in two patients with severe Parkinson's disease," *Arch. Neurol.*, 46:615-631, Jun. 1989. Published by the American Medical Association.
Widner et al., "Bilateral fetal mesencephalic grafting in two patients with Parkinsonism induced by 1-methyl-4-phenyl-1,2,3,6-tetrahydropyridine," *New Engl. J. Med.*, 327(22):1556-1563, Nov. 26, 1992. Published by the Massachusetts Medical Society.

Sortwell, et al., "Induction of Antidepressive Activity by Monoaminergic Transplants in Rat Neocortex," *Pharmacol Biochem Behav*, 46(1), pp. 225-230, 1993. Published by Pergamon Press Ltd.
Sortwell, et al., "In Vivo Release of Catecholamines from Xenogeneic Chromaffin Cell Grafts with Antidepressive Activity," *Exp Neurol* 130(1), pp. 1-8, 1994. Published by Academic Press, Inc.
Sortwell, et al., "Chromaffin cell xenografts in the rat neocortex can produce antidepressive activity in the forced swimming test," *Exp Brain Res*, 103(1) 59-69, 1995. Published by Springer-Verlag.
Fawcett, et al., "Dopaminergic neuronal survival and the effects of bFGF in explant, three dimensional and monolayer cultures of embryonic rat ventral mesencephalon," *Exp. Brain Res*. 106: 275-282, 1995. Published by Springer-Verlag.
Mehler, et al., "Cytokines and neuronal differentiation," *Crit. Rev. Neurobiol*. 9:419-446, 1995. Publisher by Begell House, Inc.
Gage, et al. "Isolation, characterization, and use of stem cells from the CNS," *Ann. Rev. Neurosci*. 18:159-92, 1995. Published by Annual Reviews Inc.
Vicario-Abejon et al., "Cerebellar precursors transplanted to the neonatal dentate gyrus express features characteristic of hippocampal neurons," *J. Neurosci*. 15(10): 6351-63, Oct. 1995. Published by Society for Neuroscience.
Suhonen et al., "Differentiation of adult hippocampus-derived progenitors into olfactory neurons in vivo," Nature 383(6601): 624-7, Oct. 17, 1996.
Ariano, et al., "Agonist-Induced Morphologic Decrease in Cellular $D_{1A}$ Dopamine Receptor Staining," *Synapse*, 27(4), pp. 313-321, 1997. Published by Wiley-Liss, Inc.
Alexander, et al., "Comparison of Neurotoxicity Following Repeated Administration of L-Dopa, D-Dopa, and Dopamine to Embryonic Mesencephalic Dopamine Neurons in Cultures Derived from Fisher 344 and Sprague-Dawley Donors," *Cell Transpl* 6(3), pp. 309-315, 1997. Published by Elsevier Science Inc.
Brustle et al., "In vitro-generated neural precursors participate in mammalian brain development," *Proc. Natl. Acad. Sci. USA Neurobiology*, 94(26): 14809-14, Dec. 1997.
McKay, "Stem cells in the central nervous system," *Science* 276(5309): 66-71, Apr. 4, 1997.
Sortwell, et al., "Pattern of synaptophysin immunoreactivity within mesencephalic grafts following transplantation in a parkinsonian primate model," *Brain Res*, 791 (1-2), pp. 117-124, 1998. Published by Elsevier.
Collier, et al., "Therapeutic potential of nerve growth factors in Parkinson's disease," *Drugs & Aging* 14(4), pp. 261-287, 1999. Published by Adis International Limited.
Collier, et al., "Diminished viability, growth, and behaviroal efficacy of fetal dopamine neuron grafts in aging rats with long-term dopamine depletion: An argument for neurotrophic supplementation," *J. Neurosci* 19(13) 5563-5573, Jul. 1, 1999. Published by Society for Neuroscience.
Sortwell, et al., "Co-Grafted Embryonic Striatum Increases the Survival of Grafted Embryonic Dopamine Neurons," *J Comp Neurol* 399(4), pp. 530-540, 1998. Published by Wiley-Liss, Inc.
Donahue et al., "Selective uptake and sustained expression of AAV vectors following subcutaneous delivery," *J Gene Med*. 1(1):31-42, 1999. Published by John Wiley & Sons, Ltd.
Wichterle et al., "Young neurons from medial ganglionic eminence disperse in adult and embryonic brain," *Nat Neurosci*, 2(5): 461-6, May 1999. Published by Nature America Inc.
Fricker et al., "Site-specific migratioin and neuronal differentiation of human neural progenitor cells after transplantation in the adult rat brain," *J Neurosci* 19(14): 5990-6005, Jul. 15, 1999. Published by Society for Neuroscience.
Ling, et al., "Striatal trophic activity is reduced in the aged rat brain," *Brain Res* 856(1-2), pp. 301-309, 2000. Published by Elsevier.
Leventhal, et al., "Cyclosporin A protects striatal neurons in vitro and In vivo from 3-nitropropionic acid toxicity," *J Comp Neurol*, 425(4), pp. 471-478, 2000. Published by Wiley-Liss, Inc.
Yamamoto, et al., "Stimulating effect of erythropoietin on the release of dopamine and acetylcholine from the rat brain slice," *Neurosci Lett* 292(2), pp. 131-133, 2000. Published by Elsevier.
Sortwell, et al., "Oligodendrocyte-type 2 astrocyte-derived trophic factors increase survival of developing dopamine neurons through the inhibition of apoptotic cell death," *J Comp Neurol* 426(1), pp. 143-153, 2000. Published by Wiley-Liss, Inc.

Studer, et al., "Enhanced proliferation, survival, and dopaminergic differentiation of CNS precursors in lowered oxygen," *J Neurosci* 20(19), pp. 7377-7383, Oct. 1, 2000. Published by Society fro Neuroscience.

Sortwell, et al., "Time course of apoptotic cell death within mesencephalic cell suspension grafts: implications for improving grafted dopamine neuron survival," *Experimental Neurology* 165(2), pp. 268-277, 2000. Published by Academic Press.

Sortwell, et al., "Diminished survival of mesencephalic dopamine neurons grafted into aged hosts occurs during the immediate postgrafting interval," *Exp Neurol* 169(1), pp. 23-29, 2001. Published by Academic Press.

Sortwell, "Strategies for the augmentation of grafted dopamine neuron survival," *Frontiers in Bioscience* 8 s522-32, May 1, 2003.

McGuire, et al., "Tumor necrosis factor $\alpha$ is toxic to embryonic mesencephalic dopamine neurons," *Exp Neurol* 169(2), pp. 219-230, 2001. Published by Academic Press.

Carvey, et al., "A Clonal line of mesencephalic progenitor cells converted to dopamine neurons by hematopoietic cytokines: A souce of cells for transplantation in Parkinson's disease," *Exp Neurol*, 171(1), pp. 98-108, 2001. Published by Academic Press.

Meltzer et al., "Serial [$^{18}$ F] fluorodeoxyglucose positron emissioin tomography after human neuronal implantation for stroke," *Neurosurgery* 49(3):586-91, Sep. 2001.

Collier, et al., "Embryonic ventral mesencephalic grafts to the substantia nigra of MPTP-treated monkeys: feasibility relevant to multiple-target grafting as a therapy for Parkinson's disease," *J Comp Neurol* 442(4), pp. 320-330, 2002. Published by Wiley-Liss, Inc.

Counts, et al., "Galanin inhibits tyrosine hydroxylase expression in midbrain dopaminergic neurons," *J Neurochem* 83(2), pp. 442-451, 2002. Published by International Society for Neurochemistry.

Dinu-Olaru, et al., "Ability of O2A progenitors to enhance survival of grafted midbrain dopamine neurons is dependent on gestational age of the donor," Program No. 691.18. 2002 Abstract Viewer/Itinerary Planner. Washington, DC: *Society for Neuroscience*, 2002. Online. (Abstract).

Kanaan, et al., "The influence of neurosphere integrity on the viability of mesencephalic progenitor cells," Program No. 34.14. 2002 Abstract Viewer/Itinerary Planner. Washington, DC: *Society for Neuroscience*, 2002. Online. (Abstract).

Marchionini, et al., "Melatonin administration enhances grafted embryonic dopamine neuron survival," Program No. 429.1. 2002 Abstract Viewer/Itinerary Planner. Washington, DC: *Society for Neuroscience*, 2002. Online. (Abstract).

McGuire, et al., "Dietary supplementation with blueberry extracts improves the survival and function of grafted embryonic dopamine neurons in rats," Program No. 787.7. 2002 Abstract Viewer/Itinerary Planner. Washington, DC: *Society for Neuroscience*, 2002. Online. (Abstract).

Sortwell, et al., "Effects of erythropoietin pretreatment on survival Of mesencephalic suspension grafts," Program No. 429.2. 2002 Abstract Viewer/Itinerary Planner. Washington, DC: *Society for Neuroscience*, 2002. Online. (Abstract).

Berkahn, et al., "In Vivo purging with rituximab prior to collection of stem cells for autologous transplantation in chronic lymphocytic leukemia," *J Hematother & Stem Cell Res* 11, pp. 315-320, 2002. Published by Mary Ann Liebert, Inc.

Rendahl et al., "Tightly regulated long-term erythropoietin expression in vivo tet-inducible recombinant adeno-associated viral vectors." *Hum Gene Ther*. 13(2):335-42, Jan. 20, 2002. Published by Mary Ann Liebert, Inc.

Maruyama et al., "High-level expression of naked DNA delivered to rat liver tail vein injection," *J Gene Med*. 4(3):333-41, 2002. Published by John Wiley & Sons, Ltd.

Auricchio et al., "Pharmacological regulation of protein expression from adeno-associated viral vectors in the eye," *Mol. Ther*. 6(2):238-42, Aug. 2002. Published by the American Society of Gene Therapy.

Terada et al., "Ligand-regulatable erythropoietin production by plasmid injectioin and in vivo electroporation," *Kidney Int*. 62(6):1966-76, 2002. Published by the International Society of Nephrology.

Samakoglu et al., "Mechanisms leading to sustained reversion of $\beta$-thalassemia in mice by doxycycline-controlled Epo delivery from muscles," *Mol Ther*. 6(6):793-803, Dec. 2002. Published by the American Society of Gene Therapy.

Hebb et al., "Glial cell line-derived neurotrophic factor-supplemented hibernation of fetal ventral mesencephalic neurons for transplantation in Parkinson disease: long-term storage," *Neurosurgical Focus*, 13(5), 2002.

Kim et al., "Differentiation of adult bone marrow stem cells into neuroprogenitor cells in vitro," NeuroReport 13(9): 1185-8, Jul. 2, 2002.

Collier, et al., "Cellular models to study dopamingergic injury responses," *Ann. N.Y. Acad Sci* 991 , p. 140-151, 2003. Published by the New York Academy of Sciences.

Pitzer, et al., "Angiogenic and neurotrophic effects of vascular endothelial growth factor (VEGF165): studies of grated and cultured embryonic ventral mesencephalic cells," *Exp. Neurol* 182(2), pp. 435-445, 2003. Published by Elsevier Science.

Marchionini, et al., "Interference with anoikis-induced cell death of dopamine neurons: implications for augmenting embryonic graft survival in a rat model of Parkinson's disease," *J Comp Neurol* 464(2), pp. 172-179, 2003. Published by Wiley-Liss, Inc.

Schwenter et al., "Optimization of human erythropoietin secretion for MLV-infected human primary fibroblasts used for encapsulated cell therapy," J. Gene Med. 5(3):246-57, 2003. Published by John Wiley & Sons, Ltd.

Johnston et al., "Regulated expression of erythropoietin from an AAV vector safely improves an anemia of $\beta$-thalassemia in a mouse model," *Mol. Ther*. 7(4):493-7, Apr. 2003. Published by The American Society of Gene Therapy.

Yanay et al., "Long-term erythropoietin gene expression from transduced cells in bioisolator devices." *Hum Gene Ther*. 14:1587-93, Nov. 20, 2003. Published by Mary Ann Liebert, Inc.

Fux et al., "Novel macrolide-adjustable bidirectional expression modules for coordinated expression of two different transgenes in mice," *J Gene Med*. 5(12):1067-79, 2003. Published by John Wiley & Sons, Ltd.

Sortwell, et al., "An in vivo interval before transplantation of mesencephalic reaggregates does not compromise survival or functionality," *Exp Neurol* 187(1), pp. 58-64, 2004. Published by Elsevier.

"LBS-Neurons for Treating Stroke," Department of Neurological Surgery, University of Pittsburg, 2004. Website: http://neurosurgery.pitt.edu/imageuided/neuron/lbsneurons, printed Jan. 6, 2003.

Marchionini, et al.; "Reassessment of caspase inhibition to augment grafted dopamine neuron survival," *Cell Transpl* 13, pp. 273-282, 2004. Published by Cognizant Comm. Corp.

Zhou et al., "The CCT promoter directs high-level transgene expression in distal lung epithelial cell lines," *Am J Respir Cell Mol Biol*. 30(1):61-8, 2004. Published by the American Thoracic Society.

Fenjves et al., "Adenoviral gene transfer of erythropoietin confers cytoprotection to isolated pancreatic islets," *Transplantation* 77(1):13-8, Jan. 15, 2004. Published by Lippincott Williams & Wilkins, Inc.

Wang et al., "Detection of integration of plasmid DNA into host genomic DNA following intramuscular injection and electroporation." *Gene Ther*. 11(8):711-21, 2004. Published by Nature Publishing Group.

Chenuaud, "Autoimmune anemia in macaques following erythropoietin gene therapy," *Blood*, 103(9):3303-4, May 1, 2004. Published by The American Society of Hematology.

Siprashvili et al., "Lentivectors for Regulated and Reversible Cutaneous Gene Delivery," *Mol Ther*. 9(1):93-100, Jan. 2004. Published by The American Society of Gene Therapy.

Herzog, "AAV-mediated gene transfer to skeletal muscle." *Methods Mol Biol*. 246:179-94, 2004. Published by Humana Press, Inc.

Grasbon-Frodi, E. M. et al., "Phenotypic Development of the Human Embryonic Striatal Primordium: A Study of Cultured and Grafted Neurons from the Lateral and Medial Ganglionic Eminences," *Neuroscience*, vol. 73, No. 1, pp. 171-183, 1996; published by Elsevier Science Ltd.

Collier, T. J. et al., Therapeutic Potential of Nerve Growth Factors in Parkinson's Disease, *Drugs & Aging*, 14 (4), pp. 261-287, 1999; published by Adis International Limited.

Potter, E. D. et al., "Cytokine-induced conversion of mesencephalic-derived progenitor cells into dopamine neurons," *Cell Tissue Res.*, vol. 296, pp. 235-246, 1999; published by Springer-Verlag.

Schierle, G. S. et al., "Differential effects of Bcl-2 overexpression on fibre outgrowth and survival of embryonic dopaminergic neurons in intracerebral transplants," *European Journal of Neuroscience*, vol. 11, pp. 3073-3081, 1999; published by European Neuroscience Association.

Yamada, M. et al., "Herpes simplex virus vector-mediated expression of Bcl-2 prevents 6-hydroxydopamine-induced degeneration of neurons in the substantia nigra in vivo," *Proc. Natl. Acad. Sci. USA*, vol. 96, pp. 4078-4083, Mar. 1999.

Holm, K. H. et al., "Enhanced Axonal Growth from Fetal Human BCL-2 Transgenic Mouse Dopamine Neurons Transplanted to the Adult Rate Striatum," *Neuroscience*, vol. 104, No. 2, pp. 397-405, 2001; published by Elsevier Science Ltd.

Natsume, A. et al., "Bcl-2 and GDNF Delivered by HSV-Mediated Gene Transfer Act Additively to Protect Dopaminergic Neurons from 6-OHDA-Induced Degeneration," *Experimental Neurology*, vol. 169, pp. 231-238, 2001; published by Academic Press.

Blum, D. et al., "Molecular pathways involved in the neurotoxicity of 6-OHDA, dopamine and MPTP: contribution to the apoptotic theory in Parkinson's disease," *Progress in Neurobiology*, vol. 65, pp. 135-172, 2001; published by Elsevier Science Ltd.

Sortwell, C. E., "Strategies for the Augmentation of Grafted Dopamine Neuron Survival," *Frontiers in Bioscience* 8, pp. 522-532, 2003.

Smith, R. et al., "Cutting Edge Communication—Embryonic Neural Progenitor Cells: The Effects of Species, Region, and Culture Conditions on Long-Term Proliferation and Neuronal Differentiation," *Journal of Hematotherapy & Stem Cell Research*, vol. 12, pp. 713-725, 2003; published by Mary Ann Liebert, Inc.

Kanaan, N. M. et al., "Exogenous erythropoietin provides neuroprotection of grafted dopamine neurons in a rodent model of Parkinson's disease," *Brain Research*, in press; published by Elsevier B.V. http://www.ncbi.nlm.nih.gov/entrez/query.fcgi?cmd=Retrieve&db=pubmed&dopt=Abstract&list_uids=16368081&query_hl=16&itool=pubmed_docsum.

* cited by examiner

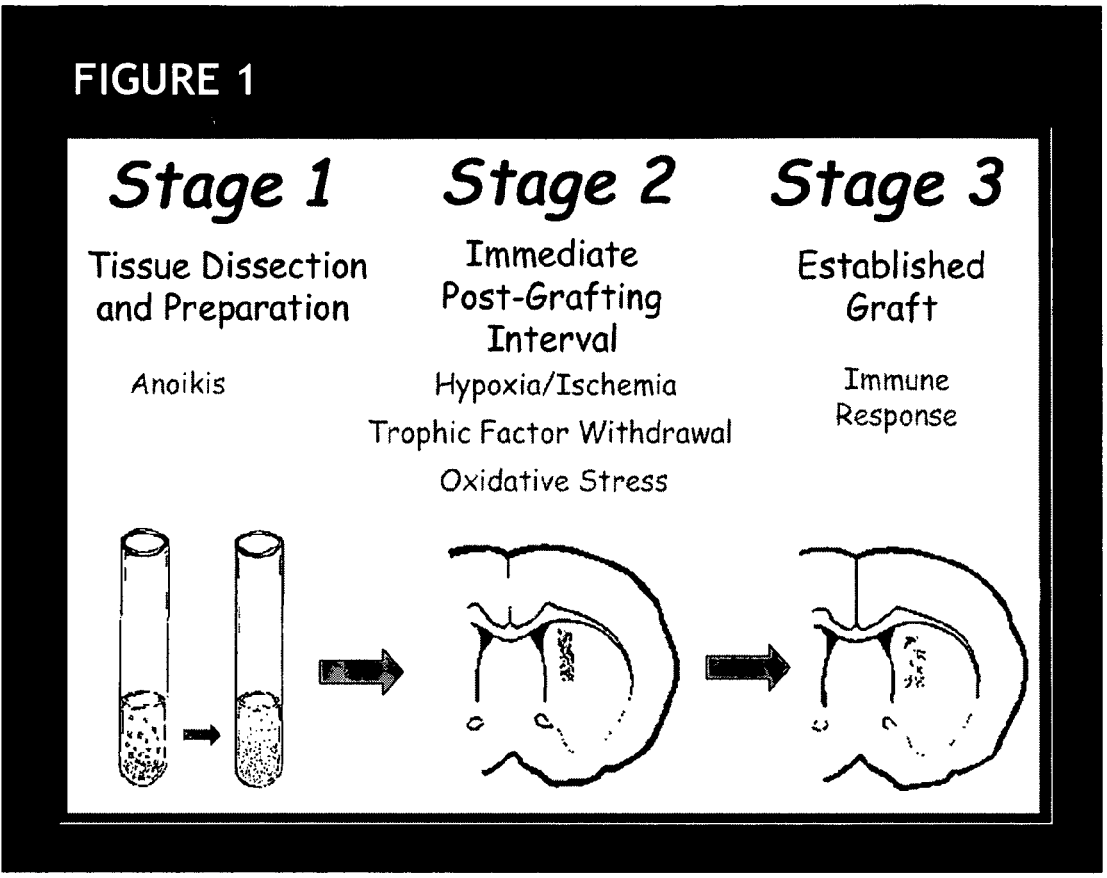

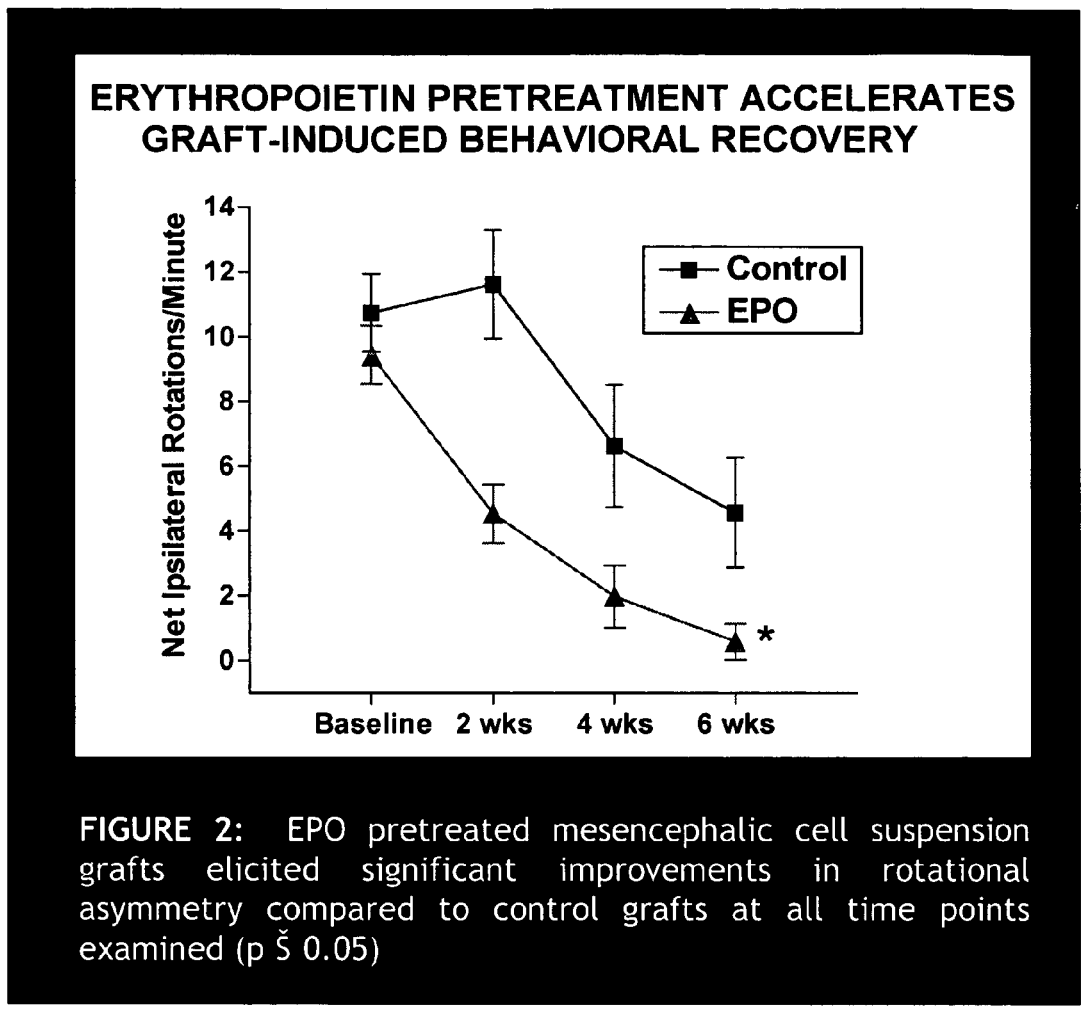
FIGURE 2: EPO pretreated mesencephalic cell suspension grafts elicited significant improvements in rotational asymmetry compared to control grafts at all time points examined (p ≤ 0.05)

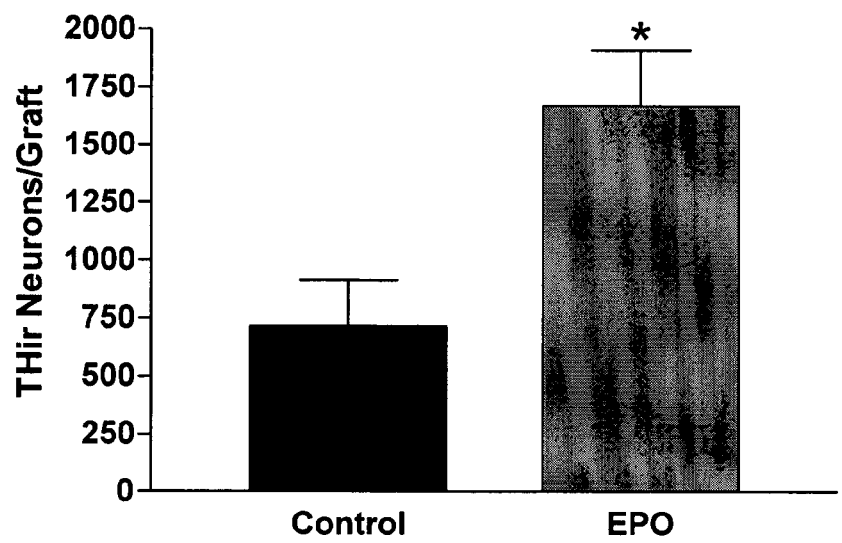
FIGURE 3: Pretreatment with EPO significantly increased grafted THir neuron survival compared to control grafts when examined at 8 weeks after implantation (p = 0.0043). Grafted THir neuron survival was increased by more than 2-fold.

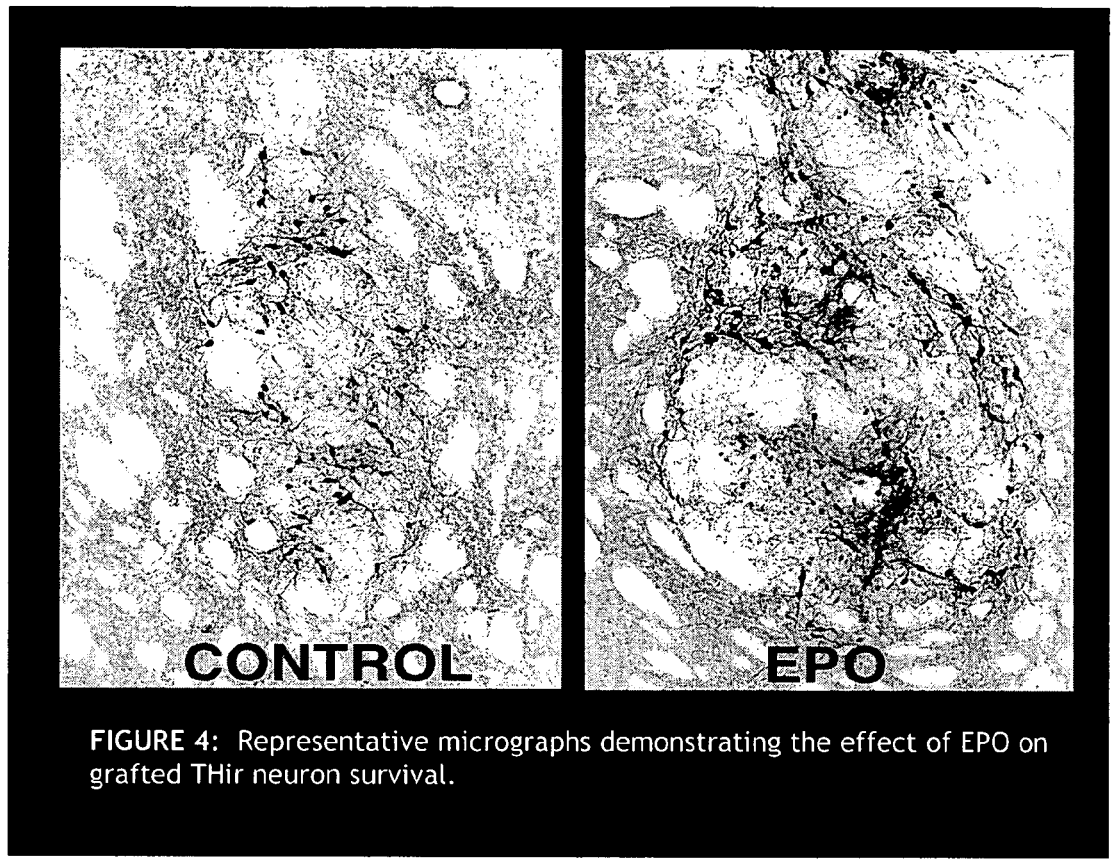
FIGURE 4: Representative micrographs demonstrating the effect of EPO on grafted THir neuron survival.

ERYTHROPOIETIN ADMINISTRATION TO IMPROVE GRAFT SURVIVAL

CLAIM OF PRIORITY

The present application claims priority to U.S. provisional patent application No. 60/464,771 filed Apr. 23, 2003, the entire contents of which are hereby incorporated by reference.

FIELD OF INVENTION

The present invention relates to increasing the survival of cell grafts. In particular, the present invention relates to increasing the survival of neurons grafted into the brain and/or spinal cord using erythropoietin or an erythropoietin analog.

BACKGROUND OF THE INVENTION

One common neurological syndrome, Parkinsonism has been the object of attempts at cell transplant therapy. Bjorklund et al., Brain Res., 177:555-560 (1979); Lindvall et al., Science, 247:574-577 (1990); Freed, Restor. Neurol. Neurosci., 3:109-134 (1991). Parkinsonism is caused by a loss of dopamine-producing neurons in the substantia nigra of the basal ganglia. Burns et al., N. Engl. J. Med., 312:1418-1421 (1985); Wolff et al., Neurobiology, 86:9011-9014 (1989). Parkinson's disease, a disease of unknown etiology which is characterized by the clinical manifestations of Parkinsonism, is caused idiopathic destruction of these dopamine-producing neurons. Parkinsonism may be caused by a variety of drugs, e.g., antipsychotic agents, or chemical agents, e.g., 1-methyl-4-phenyl-1,2,3,6-tetrahydropyridine. Burns et al., Proc. Natl. Acad. Sci. USA, 80:4546-4550 (1983) and Bankiewicz et al., Life Sci., 39:7-16 (1986).

Attempts have been made to reverse the clinical manifestations of experimentally-induced Parkinsonism by transplanting dopaminergic cells into the striatum of affected animals. Genetically modified fibroblasts (transfected with DNA encoding tyrosine hydroxylase) have been successfully transplanted into animals having lesions of dopaminergic pathways. Motor function and behavior of the animals improved following implantation of the dopamine producing fibroblasts. Wolff et al., Proc. Natl. Acad. Sci. USA, 86:9011-9014 (1989); Fisher et al., Neuron, 6:371-380 (1991). Graft survival may be enhanced, and hence clinical improvement prolonged, by transplantation of fetal tissue, as compared to cells obtained following birth. Gage and Fisher, Neuron, 6:1-12 (1991). Fresh fetal dopaminergic neurons have been transplanted into the caudate nucleus of monkeys following chemical injury to the nigrostriatal dopamine system. Following transplantation, the injury-induced behavioral deficits improved. Bankiewicz et al., J. Neurosurg., 72:231-244 (1990) and Taylor et al., Prog. Brain Res., 82:543-559 (1990). Humans suffering from Parkinsonism have been treated by striatal implantation of dopaminergic neurons. Lindvall et al., Arch. Neurol., 46:615-631 (1989); Widner et al., New Engl. J. Med., 327:1556-1563 (1992). However, these treatments have been hampered by the high rate of cell death that occurs in the transplanted cells. In fact, it is estimated that as little as 5-10% of the cells survive upon transplantation.

Thus, there remains a need to increase the survival of grafted cells, in particular a need to increase the survival of cells used to treat neurological diseases.

SUMMARY OF THE INVENTION

The present invention provides methods, compounds and kits for increasing the survival of cell grafts. One of these embodiments provides a method for increasing the survival of cells in a tissue graft. This method includes at least the following steps:
(a) contacting a tissue graft with an effective amount of exogenous erythropoietin (EPO) or an analog of EPO; and
(b) administering the tissue graft into a compatible recipient tissue. In these methods the survival of cells in the tissue graft is increased compared to cells in a tissue graft not contacted with EPO or an analog thereof. In other of these methods, when (a) occurs prior to (b) then the tissue is graft is preferably made up of differentiated cells. Additionally, in some embodiments, when (a) occurs simultaneous with or subsequent to (b) then the tissue graft is not an endothelial graft, endothelial progenitor graft, vascular graft or skin graft. In these methods, (a) can occur prior, simultaneous with and/or subsequent to (b). The present methods can also include obtaining the tissue graft prior to (a). In some embodiments the tissue graft is a neuronal tissue graft. In these and other embodiments, the compatible tissue is part of the nervous system of a patient, such as brain tissue or spinal cord tissue. In certain methods, the cells of the tissue graft include dopamine producing neurons, acetylcholine producing cells, cells that produce gamma amino butyric acid, cells that produce molecules which block excitatory amino acid pathways and mixtures thereof. In some of the methods, (b) can be include by injecting a suspension of cells into the compatible recipient tissue. The recipient tissue can be in vivo. Other methods of the present invention can treat a neurological injury, disease or disorder and include:
(a) contacting a tissue graft with an effective amount of exogenous erythropoietin (EPO) or an analog of EPO or administering the EPO or an analog of EPO to the cells of the tissue graft; and
(b) administering the tissue graft into a compatible recipient neuronal tissue. In these methods, the survival of cells in the tissue graft is increased compared to cells in a tissue graft not contacted with EPO or an analog thereof. In some of the methods, the neurological injury, disease or disorder can be Parkinsonism, Alzheimer's disease, Huntington's chorea, multiple sclerosis, amyotrophic lateral sclerosis, Gaucher's disease, Tay-Sachs disease, a neuropathy, a brain tumor, a traumatic brain injury, a spinal cord injury or a stroke injury. In these methods, (a) can occur prior, simultaneous with and/or subsequent to (b). The present methods can also include obtaining the tissue graft prior to (a). The tissue graft can also be a neuronal tissue graft and the compatible recipient neuronal tissue can be brain tissue or spinal cord tissue. In any of the methods described herein, the EPO or EPO analog can be recombinant human protein. Additionally, the cells of the tissue graft can include dopamine producing neurons, acetylcholine producing cells, cells that produce gamma amino butyric acid, cells that produce molecules which block excitatory amino acid pathways and mixtures thereof.

In some embodiments, administering the EPO or an analog of EPO to the cells of the tissue graft can involve inducing the cells to increase the level of EPO or EPO analog. Increased EPO levels can be induced by hypoxia of the cells, gene therapy, nucleic acid delivery, or the like.

Objects and advantages of the present invention will become more readily apparent from the following detailed description.

BRIEF DESCRIPTION OF THE DRAWINGS

FIG. 1 is a summary of specific threats to grafted neuron survival;

FIG. 2 shows the average number of net ipsilateral rotations per minute between grafts of freshly suspended ventral mesencephalic cells pretreated for 30 minutes with 20 IU/ml erythropoietin or mesencephalic cells pretreated with delivery vehicle only;

FIG. 3 shows a comparison in survival rates of grafted tyrosine hydroxylase immunoreactive (THir) neurons between grafts of EPO— pretreated mesencephalic cells and control non-pretreated mesencephalic cells; and FIG. 4 shows representative micrographs demonstrating the effect of EPO on grafted tyrosine hydroxylase immunoreactive neuron survival.

DETAILED DESCRIPTION OF PREFERRED EMBODIMENTS

The percentage of grafted embryonic dopamine (DA) neurons that survive delivery is low, estimated at 5-10%. Cell death by either apoptosis or necrosis drastically reduces the yield of viable grafted neurons, however, the significant contribution of apoptotic cell death offers specific avenues for intervention. A summary of specific threats to grafted neuron survival is shown in FIG. 1.

The present invention provides methods, compounds and kits that increase the survival of cell grafts that are implanted into a defect site. Generally, the present invention involves conditioning the cells of a cell graft with an effective amount of exogenous erythropoietin (EPO) or an analog thereof to increase the survival of the administered cells. As used herein, an effective amount of the EPO and/or analog thereof refers to an amount or concentration that increases the survival of the transplanted cells relative to a control or transplant that has not been treated with the EPO and/or analog thereof, and one skilled in the art will realize that such comparison need not actually be performed in order to practice the present invention. EPO can be administered, e.g levels of EPO in cells can be increased, by subjecting the cells to hypoxic conditions, such as discussed in U.S. Pat. Nos. 5,750,376, 6,368,854 and 6,638,501, or through gene transfer or genetic engineering. These methods can be used to induce the cells to produce increased amounts of EPO or the EPO analog. In one embodiment, the cell graft can be genetically modified ex vivo to produce EPO or an EPO analog via gene transfer utilizing adeno, adenoassociated, herpes simplex or lenti viral vectors. Suitable vectors, gene transfer agents, naked nucleic acid and methods for erythropoietin are discussed by Donahue et al., J Gene Med. 1999 January-February; 1(1):31-42, Rendahl et al., Hum Gene Ther. 2002 Jan. 20; 13(2):335-42, Maruyama et al., J Gene Med. 2002 May-June; 4(3):333-41, Auricchio et al., Mol Ther. 2002 August; 6(2):238-42, Terada et al., Kidney Int. 2002 December; 62(6):1966-76, Samakoglu et al., Mol Ther. 2002 December; 6(6):793-803, Schwenter et al., Gene Med. 2003 March; 5(3):246-57, Johnston et al., Mol Ther. 2003 April; 7(4):493-7, Zhou et al., Am J Respir Cell Mol. Biol. 2004 January; 30(1):61-8, Yanay et al., Hum Gene Ther. 2003 Nov. 20; 14(17):1587-93, Fux et al., J Gene Med. 2003 December; 5(12):1067-79, Fenjves et al., Transplantation. 2004 Jan. 15; 77(1):13-8, Wang et al., Gene Ther. 2004 April; 11(8):711-21, Chenuaud, Blood. 2004 May 1; 103(9):3303-4, Siprashvili et al., Mol Ther. 2004 January; 9(1):93-100, Herzog, Methods Mol. Biol. 2004; 246:179-94.

EPO is a glycoprotein hormone that is produced by the body to regulate blood cell production and is produced mainly in the kidney of an adult and in the liver of a fetus. Thus EPO is most often understood in terms of its effects on stimulating erythropoiesis. EPO is also an inducible cytokine which is produced in the brain in response to hypoxia. EPO protein and EPO receptor are expressed throughout the brain, including the mesencephalon, from development through adulthood.

As used herein an "analog of EPO," "EPO analog," or the like refers to a compound that binds to the receptor for EPO and induces a response akin to that elicited when EPO binds an EPO receptor. Examples of such EPO analogs include, without limitation, EPO isoforms, EPO which has been engineered or chemically modified to increase its bioavailability or stability, and peptides that bind the EPO receptor. Specific examples of suitable analogs include darbepoietin alpha (Aranesp®) available from Amgen Inc., Thousand Oaks, Calif.), and those disclosed In U.S. Pat. Nos. 5,986,047, 5,888,772, 5,856,298, 5,830,851 and 5,773,569 and WO 94/25055.

Synthetic and recombinant versions of EPO are also suitable for use in the present methods and compounds. In some embodiments, the EPO is human EPO, and preferably recombinant EPO, such as Epoetin alpha, distributed as PROCRIT® by Ortho Biotech Products (Bridgewater, N.J.) or by Amgen as Epogen®. Various procedures for producing EPO are known and include those discussed in U.S. Pat. Nos. 5,955,422, 5,756,349, 5,621,080, 5,618,698, 5,547,933, 5,441,868 and 4,703,008. In one embodiment the EPO is human EPO or human recombinant EPO.

In one embodiment, the present methods involve culturing cells of a cell graft in the presence of an effective amount of EPO or an analog thereof prior to delivery of the cell graft into a compatible recipient tissue thereby increasing a survival rate of cells of the tissue graft, particularly once the cells have been administered. This preculture or preconditioning of the cells can involve culturing the cells that are to be delivered with the EPO or analog thereof for a relatively short period of time, for example 15 to 30 minutes, or can involve more prolonged periods of culture, such as those lasting 1, 2, 3, or more days. Generally, the EPO or analog thereof will be in the same medium as the cell graft up until the time the cells are administered into the compatible recipient tissue. As used herein a compatible tissue means a tissue which is capable of incorporating the cells of the cell graft and receiving a benefit from successfully grafted cells. For example, when neuronal cells make up part of the cell graft then a compatible tissue can be nervous system tissue, such as brain or spinal cord tissue or when the cell graft includes muscle cells then the compatible tissue can be muscle tissue. Other cells that can be used in the present methods include, without limitation, stem cells, neural stem cells, neural progenitor cells, oligodendrocyte-type 2 astrocyte progenitor cells, astrocytes, oligodendrocytes, primary neurons (embryonic or adult), fibroblasts, chromaffin cells, motor neurons, pancreatic islet cells, Schwann cells, carotid body cells, Sertoli cells, kidney cells, BHK cells, and various cell lines (SHY cells, HNT cells, PC 12 cells). In some embodiments, the cells will not be stem cells, neural stem cells, multipotent neural stem cells, neural progenitor cells, and oligodendrocyte astrocyte progenitor cells, such as the cells disclosed in U.S. Pat. Nos. 5,750,376, 6,368,854 and 6,638,501. Generally the survival rate is compared to a survival rate of cells of a control tissue graft not cultured with the EPO or analog thereof. The preculture of the cells can also be used to increase the viability of stored cells thereby enabling longer storage periods of graft material. Typically, a decline in human fetal ventral mesencephalon tyrosine hydroxylase-positive cell survival is seen beyond 3 days in cool storage. Hebb et al., Neurosurgical Focus, Vol. 13, No. 5 (2002). However, this decline may be overcome or ameliorated by preculturing of the cells with the EPO or analog thereof. It is contemplated that the present treatment can prolong the survival of these cells for up to 7, 8 or 9 days.

In one embodiment, the cell graft can be administered into the desired tissue and then the EPO or analog thereof can be administered to the patient receiving the graft. In some embodiments, the EPO or analog thereof can be administered to the graft recipient systemically, although generally the EPO or analog thereof will be selectively administered to the area of the cell graft to increase the survival of the grafted cells. In this embodiment, administration of the EPO or analog thereof can occur once, several times or can be performed continuously. Generally administration of the EPO or analog thereof will continue until the cells have become successfully engrafted into the recipient tissue which can occur 7-10 days post-administration.

Similarly, the EPO or analog thereof can be administered to the site where the cells are grafted simultaneously with the administration of the cell graft to the compatible tissue. EPO can also be used at a multiple of the different stages of the grafting procedure, including in the culture of the cells to be grafted, simultaneous with the cell graft and/or subsequent to the graft. In some embodiments, the EPO or analog thereof can be together in composition with the tissue graft and the composition can be administered to a recipient.

Generally, the EPO or analog thereof will be present in the culture media or administered in an effective amount, i.e. an amount which increases the survival of the cells administered into the recipient tissue. More specifically, the EPO or analog thereof can be present in amount of at least 0.001 IU/mL, and for example in an amount of 0.001 to 100 IU/mL, such as 0.001, 0.01, 0.1, 1, 2, 5, 7, 10, 15, 20 or 25 to 30, 35, 50, 80 IU/mL. Concentrations of EPO up to 160 IU/ml have been successfully used in culture with no apparent cytotoxicity. Higher concentrations of EPO can also be used in the present invention, such as for example up to 150, 200, 250, 300, 350, 400, 450, 500 IU/mL or more.

As will be understood by one skilled in the art, for any and all purposes, particularly in terms of providing a written description, all ranges disclosed herein also encompass any and all possible subranges and combinations of subranges thereof. Accordingly, EPO in an amount of at least 10 nM includes 12 nM, 17.5 nM, etc. as well as all included ranges such as 20 to 200 nM, 10 to 75 nM, etc. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

The methods of tissue grafting and administration described herein can involve the use of solid pieces of tissue implanted directly into the recipient tissue. However, solid pieces of tissue cannot be implanted and sustained in all tissues and thus solid pieces of tissue can be disaggregated to provide cell grafts that include suspensions of individual cells or small clusters of cells. This cell suspension can then be directly implanted, typically via injection, into the recipient tissue. As will be understood by the skilled artisan, the cells should be suspended in a suitable medium that maintains the viability of the dissociated cells. Using cell suspensions provides several advantages for the delivery procedure, including easier manipulation, expansion, monitoring and/or culture of the cells. Additionally, cells in suspension are believed to become more easily integrated into the recipient tissue and may provoke a less severe immune response. Using cell cultures also allows for increased homogeneity of cells as well as providing a single source of cells that can be continually expanded to provide an inexhaustible source of donor cells for grafting. As one of skill in the art will readily understand, the ability for tissues to be easily dissociated may depend on the type of cell being used. Methods for grafting of neuronal cells are disclosed, for example, in U.S. Pat. Nos. 6,497,872; 6,444,205 and 5,750,376. The cells used in the present invention as well as the EPO or analog thereof can be encapsulated into a compatible matrix. This matrix will generally be biodegradable and can facilitate handling and delivery of the cells and EPO and analogs thereof.

Generally, the cell graft involves an amount of cells sufficient to provide a population of cells that survives and provides relief of or abatement of the desired condition. The number of cells needed to achieve the purposes of the present invention is variable depending on the size, age, weight of the subject, the nature of the underlying disease, disorder or condition, other concurrent therapies, and the like. The number of cells needed will also depend upon the type of cell being used in the cell graft. The number of cells needed can be determined by one of skill in the art without undue experimentation. In an adult human, an effective number of cells is in the range of about $1\times10^3$ to about $1\times10^9$ cells, including about $5\times10^3$ to about $1\times10^6$ cells or about $1.5\times10^5$ to about $3\times10^6$ cells. Generally, grafts in humans can utilize about 3,000,000 dopaminergic cells per graft, whereas animal studies routinely use between 150,000-1,000,000 dopaminergic cells per graft. In some embodiments, the effective amount of administered cells can be determined in terms of mass of cells. In general, the number of cells administered can provide a final number of surviving grafted cell on the order of approximately 100,000 to 150,000 cells. For most clinical applications, cells will be administered as part of a pharmaceutically acceptable composition such as those disclosed in U.S. Pat. No. 6,451,306. Multiple cell grafts, such as 2, 3, 4, 5, 10 or more cell grafts can also be performed by the present methods.

The present methods can also involve subjecting the cells of the graft to hypoxic insult which increases EPO and EPO receptor production in the cells of the graft. After exposure to severe hypoxia, EPO mRNA is upregulated by both astrocytes and neurons. Following ischemic insult, the EPO receptor is upregulated on cells within the penumbra.

In some embodiments, the grafts described herein are neural grafts, which refers to the administration of tissue into the brain or spinal cord. Neural grafts can provide a source of depleted chemical substances, stimulate neuron growth, promote survival of neurons, and replace lost or damaged structures in the brain and spinal cord.

For implantation of the cells into the brain, stereotaxic methods are generally used (See e.g., Leksell and Jemberg, Acta Neurochir. 52:1 (1980); and Leksell et al., J. Neurosurg. 66:626 (1987)). Methods for administering cells to specific regions of the central nervous system are taught by U.S. Pat. No. 5,650,148, incorporated herein by reference. These neural delivery, e.g., transplantation or "grafting," methods involve administering cells into the central nervous system or into the ventricular cavities or subdurally onto the surface of a host brain. Considerations for successful engraftment include: 1) viability of the implant; 2) retention of the graft at the site of administration; and 3) minimum amount of pathological reaction at the site of administration.

Methods for administering various nerve tissues have been described in Neural Grafting in the Mammalian CNS (Bjorklund and Stenveni, eds. (1985)); Das, Ch. 3 pp. 23-30; Freed Ch. 4, pp. 31-40; Stenevi et al., Ch. 5, pp. 41-50; Brundin et al., Ch. 6, pp. 51-60; David et al., Ch. 7, pp. 61-70; and Seiger, Ch. 8, pp. 71-77, herein incorporated by reference. In some grafting embodiments, the cell suspension is drawn up into a syringe and administered to anesthetized graft recipients. Multiple injections may be made using this procedure at either the same site or different sites.

The use of cellular suspension procedures provides many advantages. For example, these methods permit grafting cells to any predetermined site in the brain or spinal cord, are relatively non-traumatic, allow multiple grafting simultaneously in several different sites or the same site using the same cell suspension, and permit the use of mixed cells obtained from different anatomical regions. Preferably, from approximately $10^4$ to approximately $10^8$ cells are introduced per graft, although certain applications and certain cell types may require higher or lower numbers.

Typically, the number of cells administered into the patient or host will be a "therapeutically effective amount." As used herein, "therapeutically effective amount" refers to the number of administered cells that are required to effect treatment of the particular disorder for which treatment is sought. For example, where the treatment is for Huntington's disease, administration of a therapeutically effective amount of cells will typically produce a reduction in the amount and/or severity of the symptoms associated with Huntington's disease. Persons of skill in the art will understand how to determine proper cell dosages.

Survival of the administered cells can be determined by any suitable method. One non-limiting method includes recording the number of fetal mesencephalons pooled for dissociation during mesencephalic tissue dissection and dissociation procedures so that an average number of dissociated cells per mesencephalon can be determined. Previous studies have estimated that each fetal mesencephalon (at the age of dissection) possesses an average of 37,500 dopaminergic neurons (Fawcett et al., Exp. Brain Res. 106: 275-282 (1995)) as determined by immunocytochemical staining for tyrosine hydroxylase, the rate limiting enzyme for dopamine synthesis. Therefore, by knowing the number of cells per mesencephalon, the average number of dopaminergic neurons per mesencephalon and the total number of mesencephalic cells initially grafted one can calculate the number of dopaminergic neurons implanted. Grafted dopaminergic cell survival is then calculated postmortem via staining for tyrosine hydroxylase using serial brain sections through the graft that are counted according to Abercrombie's formula or using stereology. These calculations can provide total tyrosine hydroxylase positive cell number per graft. This number is then compared to the number of tyrosine hydroxylase positive cells initially grafted to determine grafted dopaminergic neuron survival rate. Survival of the graft in the living host can also be examined using various non-invasive scans such as computerized axial tomography (CAT scan or CT scan), nuclear magnetic resonance or magnetic resonance imaging (NMR or MRI) or positron emission tomography (PET) scans. Post-mortem examination of graft survival can be done by removing the neural tissue, and examining the affected region macroscopically, or using microscopy. Cells can be stained with any stain visible under light or electron microscopic conditions, more particularly cells can be stained with stains which are specific for neurons and glia. Particularly useful are monoclonal antibodies that identify neuronal cell surface markers such as the M6 antibody, which identifies mouse neurons. Most preferable are antibodies which identify any neurotransmitters, particularly antibodies directed to GABA, TH, ChAT, and substance P, and antibodies directed to enzymes involved in the synthesis of neurotransmitters, in particular, GAD. Delivered cells can also be identified by prior incorporation of tracer dyes such as rhodamine- or fluorescein-labeled microspheres, fast blue, bisbenzamide or retrovirally introduced histochemical markers such as the lac Z gene, which produces beta galactosidase. Lactate dehydrogenase release can also be measured as an indicator of cell death. Tyrosine hydrolase immunoreactivity can also be used to assess graft survival.

Functional integration of the graft into the host's neural tissue can be assessed by examining the effectiveness of grafts on restoring various functions, including but not limited to tests for endocrine, motor, cognitive and sensory functions. Motor tests which can be used include those which quantitate rotational movement away from the degenerated side of the brain, and those which quantitate slowness of movement, balance, coordination, akinesia or lack of movement, rigidity and tremors. Cognitive tests include various tests of ability to perform everyday tasks, as well as various memory tests, including maze performance.

In the above embodiments, the EPO or analog thereof can be administered either to the cell culture or graft site prior to substantial vascularization of the tissue graft. As used herein "substantial vascularization" means the time at which the grafted tissue has developed a vascular system sufficient to support the viability of the surviving cells in the tissue graft. Generally prior to this time period vascularization, and accordingly blood flow, is insufficient to support the continued viability of the live cells residing in the grafted tissue. As understood by the skilled artisan, this time period can be readily determined using only routine experimentation but has no set value and will depend on many factors, including speed of healing, administration of promoters or inhibitors of vascularization, identity of the grafted tissue, size of the tissue graft, age of the patient, and other factors recognized by the skilled.

Surprisingly and unexpectedly, the survival rate of the cells of a tissue graft treated with EPO or an analog thereof has resulted in increased survival of the cells of the graft compared to a control tissue graft in which the cells were not treated with EPO or an analog thereof. In fact, survival rates that were roughly 2-fold or greater than that of a control graft have been achieved using the present methods. Although the present methods have achieved such increased survival rates, the present invention is also capable of achieving more modest survival rates, such as an increase of 10%, 20%, 50%, 75% or more compared to a control. It is also expected that survival rates that are 3, 4, 5, 6 or even 10 fold greater can be achieved by the present methods. As will be apparent to the skilled artisan, an actual comparison of the survival rates need not be performed in order to practice the present invention, but rather a control sample which has not been exposed to EPO or an analog thereof can be used to gauge the effectiveness of the EPO administration.

In some embodiments, an initial stage for any cell or tissue grafting can lie in obtaining or isolating the cells that have a desired characteristic and which are to be used in the tissue graft. In the present methods the cells making up the tissue to be grafted are not particularly limited. Accordingly, a tissue graft may be derived from various types of tissues and cells, including fetal tissue, peripheral nervous tissue, cells from various organs, or cell lines sustained in the laboratory. Additionally, genetically engineered cells can be used for the tissue graft. In some embodiments, the cells for grafting are neuronal cells which can be obtained from brain or spinal cord tissue.

A number of different cell types are useful for the present invention. In some embodiments, a cell will be selected based on its ability to provide a substance that is absent or decreased relative to normal levels in the recipient brain. Missing substances can be neurotransmitters or other neurally-active molecules, such as peptides, the absence of which results in neurological disease or dysfunction. It is preferred that the administered cell not grow as a tumor once it is inserted into the recipient. Suitable sources of cells include those that provide stem cells, neural stem cells, neural progenitor cells, oligodendrocyte-type 2 astrocyte progenitor cells, astrocytes, oligodendrocytes, primary neurons (embryonic or adult), fibroblasts, chromaffin cells, motor neurons, pancreatic islet cells, Schwann cells, carotid body cells, Sertoli cells, kidney cells, BHK cells, and various cell lines known in the art, such as SHY cells, HNT cells and/or PC12 cells.

The cells can also be expanded to produce the desired numbers of cells. The cells can also be cultured using the EPO or analog thereof to condition the cells for administration and facilitate the increased survival of the cells, upon being grafted into the recipient tissue. To expand a population of neural cells, (e.g., progenitor cells) the cells can be grown in the presence of trophic factors, such as nerve growth factor, acidic fibroblast growth factor, basic fibroblast growth factor, platelet-derived growth factor, thyrotropin releasing hormone, epidermal growth factor, amphiregulin, transforming growth factor, transforming growth factor-beta, insulin-like growth factor, glial cell line-derived neurotrophic factor or other growth factors using methods known in the art (see, e.g., U.S. Pat. Nos. 5,753,506; 5,612,211; 5,512,661; and WO93/01275; Mehler et al. 1995 Crit. Rev. Neurobiol. 9:419; and WO 98/30678).

The cells useful in the methods of the present invention may be xenogeneic (heterologous, i.e., derived from a species different from the recipient), allogeneic (homologous, i.e., derived from a genetically different member of the same species as the recipient) or autologous, wherein the recipient also serves as the donor.

In the case of a heterologous donor animal, the animal may be euthanized, and the neural tissue and specific area of interest removed using a sterile procedure. Areas of particular interest include any area from which neural cells can be obtained that will serve to restore function to a degenerated area of the host's nervous system, particularly the host's CNS. Suitable areas include the cerebral cortex, cerebellum, midbrain (mesencephalon), brainstem, spinal cord, and ventricular tissue, and areas of the PNS including the carotid body and the adrenal medulla. Preferred areas include regions in the basal ganglia, preferably the striatum, which consists of the caudate and putamen, or various cell groups such as the globus pallidus, the subthalamic nucleus, the nucleus basalis which is found to be degenerated in Alzheimer's Disease patients, or the substantia nigra pars compacta or mesencephalic cells which are found to be degenerated in Parkinson's Disease patients. Particularly preferred neural tissue is obtained from ventricular tissue that is found lining CNS ventricles and includes the subependyma. The term "ventricle" refers to any cavity or passageway within the CNS through which cerebral spinal fluid flows. Thus, the term not only encompasses the lateral, third, and fourth ventricles, but also encompasses the central canal, cerebral aqueduct, and other CNS cavities. These areas in the recipient tissue are also suitable targets for receiving the tissue grafts.

Human heterologous neural cells may be derived from fetal tissue following elective abortion, or from a post-natal, juvenile or adult organ donors. Autologous neural tissue can be obtained by biopsy, or from patients undergoing neurosurgery in which neural tissue is removed, for example, during epilepsy surgery, temporal lobectomies and hippocampalectomies. Neural cells have been isolated from a variety of adult CNS ventricular regions, including the frontal lobe, conus medullaris, thoracic spinal cord, brain stem, and hypothalamus, and proliferated in vitro using the methods discussed in U.S. Pat. No. 6,497,872. Suitable cells for administration can come from established cell lines that have specific properties. These cells can include any dopaminergic cell line including dopaminergic progenitor cells, SHY cells or cell lines genetically engineered to release dopamine, as well as stem cells, neural stem cells, neural progenitor cells, oligodendrocyte-type 2 astrocyte progenitor cells, astrocytes, oligodendrocytes, fibroblasts, chromaffin cells, motor neurons, pancreatic islet cells, Schwann cells, carotid body cells, Sertoli cells, kidney cells and/or BHK cells.

Many studies utilizing grafts of stem and precursor cells have yielded results suggesting that the default differentiation pathway of undifferentiated stem/precursor cells is toward the phenotype of neurons endogenous to the site of grafting (Brustle et al., 1997; Gage et al., 1995; McKay 1997; Suhonen et al., 1996; Vicario-Abejon et al., 1995a; Wichterle et al., 1999). However, many delivery paradigms utilize heterotopic placement strategies, meaning that cells are grafted not to their original in situ location, but rather to the target fields of these cells. The best example of this is the practice of implanting dopamine neurons to the striatum rather than to the substantia nigra. Most of the cells in the striatum are GABAergic and undifferentiated stem cell grafts to the striatum have been demonstrated to differentiate into a GABAergic phenotype rather than dopaminergic (Fricker et al., 1999). These findings have led many researchers to predifferentiate stem or progenitor cells towards the desired phenotype prior to implantation (Carvey et al., 2001; Kim et al., 2002). Depending on the differentiation protocol, stem or precursor cells are transfected with genes of interest and/or exposed to cytokines that drive the generation of the desired neuron type. Phenotype is then confirmed in culture prior to implantation. Therefore, while these cells were originally stem or precursor cell-derived, at the time of grafting they are mature, differentiated, post-mitotic neurons. In some embodiments, it is at this differentiated stage that they would be exposed to EPO or an analog thereof to promote cell survival after grafting. As such, the present methods can utilize stem cells that are subjected to the conditions described above, or EPO, an EPO analog or hypoxic insult to promote differentiation as discussed in U.S. Pat. No. 6,165,783, followed by administration of EPO or an analog thereof to the differentiated cells used thereby increasing the survival of the differentiated cells upon grafting.

Administration can be done bilaterally, or, in the case of a patient suffering from certain conditions, such as Parkinson's Disease, contralateral to the most affected side. Surgery is performed in a manner in which particular brain regions may be located, such as in relation to skull sutures, particularly with a stereotaxic guide. Cells are delivered throughout any affected neural area, in particular to the basal ganglia, and preferably to the caudate and putamen, the nucleus basalis or the substantia nigra. Cells are administered to the particular region using any method which maintains the integrity of surrounding areas of the brain, preferably by injection cannula. Injection methods exemplified by those used by Duncan et al. J. Neurocytology, 17:351-361 (1988), and scaled up and modified for use in humans are preferred. Methods taught by U.S. Pat. No. 5,082,670, for the injection of cell suspensions such as fibroblasts into the CNS may also be employed for injection of neural precursor cells. Additional approaches and methods may be found in Neural Grafting in the Mammalian CNS, Bjorklund and Stenevi, eds., (1985).

Neural cells when administered to the particular neural region preferably form a neural graft, wherein the neuronal cells form normal neuronal or synaptic connections with neighboring neurons, and maintain contact with administered or existing glial cells that may form myelin sheaths around the neurons' axons, and provide a trophic influence for the neurons. As these administered cells form connections, they reestablish the neuronal networks that have been damaged due to disease, aging or injury.

In some embodiments of the present invention, the graft is not an endothelial graft, endothelial progenitor graft, vascular graft or skin graft. More particularly, the methods of EPO or EPO analog administration are used to increase survival of the grafted cells not to prevent or stop bleeding or promote chemotaxis of cells. In some of the embodiments described herein, when the cells of the graft are cultured with EPO or an analog thereof prior to administration the cells are differentiated cells. In other embodiments where preculture with EPO or EPO analog is used the EPO or EPO analog should be present in the tissue graft when the graft is implanted into the recipient tissue. As used herein, the term neural stem cell, such as a multipotent or oligopotent cell, refers to an undifferentiated cell which is capable of self-maintenance. Thus, in essence, a stem cell is capable of dividing without limit. The non-stem cell progeny of a multipotent neural stem cell are termed "progenitor cells." A distinguishing feature of a progenitor cell is that, unlike a stem cell, it has limited proliferative ability and thus does not exhibit self-maintenance. It is committed to a particular path of differentiation and will, under appropriate conditions, eventually differentiate. A neuronal progenitor cell is capable of a limited number of cell divisions before giving rise to differentiated neurons. A glial progenitor cell likewise is capable of a limited number of cell divisions before giving rise to astrocytes or oligodendrocytes. A neural stem cell is multipotent because its progeny include both neuronal and glial progenitor cells and thus the neural stem cell is capable of giving rise to neurons, astrocytes, and oligodendrocytes. Methods of obtaining neural precursor cells, e.g., neural stem cells and/or progenitor cells are known in the art, e.g., U.S. Pat. No. 5,753,506; WO 97/44442; WO 96/04368; WO 94/10292; WO9 4/02593; Gage et al. 1995 Ann. Rev. Neurosci. 18:159; or WO98/30678, the contents of which are incorporated herein by reference. Where neural stem cells are used, they are generally differentiated prior to treatment with the EPO or analog thereof or administration.

In some embodiments, the cells of the tissue graft are progenitor cells or differentiated cells, such as neuronal cells including dopamine producing neurons.

The present methods can also use cells which are frozen and stored in a frozen state using methods well known in the art. Following thawing, the cells can be implanted into a recipient brain. The frozen cells can be treated with the EPO or analog thereof prior to or after freezing or thawing.

A wide variety of diseases and syndromes may be treated by the methods of the present invention. Generally, the disease will be a neurological disease, such as Parkinsonism (including Parkinson's disease), Alzheimer's disease, Huntington's chorea, multiple sclerosis, amyotrophic lateral sclerosis, Gaucher's disease, Tay-Sachs disease, neuropathies, brain tumors, traumatic brain or spinal cord injury and the like. The present invention can also be used to treat stroke injury. In particular, use of LBS-neurons can be used as cell grafts for the treatment of stroke. Meltzer et al., Neurosurgery 2001 September; 49(3):586-91. The methods of the present invention may also be employed in the treatment of non-neurological diseases.

Parkinson's Disease can be treated according to the present invention by implanting mesencephalic or dopamine-producing cells in the recipient's striatum. Dopaminergic neurons can be obtained from existing cell lines, such as primary DA neurons from the fetal mesencephalic tissue or stem/progenitor-derived DA neurons and those disclosed in U.S. Pat. Nos. 6,395,546, 6,284,539 and 6,277,820. Accordingly, graft sites for Parkinson's disease can include include caudate, putamen, substantia nigra (any structure of the nigro-striatal system,) and the cortex. Alzheimer's disease involves a deficit in cholinergic cells in the nucleus basalis. Thus, according to the invention, a subject having Alzheimer's disease or at risk therefor may be implanted with cells producing acetylcholine. Graft sites for Alzheimer's disease include the basal forebrain, the cortex, hippocampus, and the locus coeruleus and raphe nuclei. Huntington's disease involves a gross wasting of the head of the caudate nucleus and putamen, usually accompanied by moderate disease of the gyrus. A subject suffering from Huntington's disease can be treated by implanting cells producing the neurotransmitters gamma amino butyric acid (GABA), acetylcholine, or a mixture thereof. See, for example, U.S. Pat. No. 6,254,865. Graft sites for Huntington's disease can include the basal ganglia structures and the cortex. Concerning other diseases and injuries, graft sites for ischemia can include any CNS or PNS area with ischemic damage. Graft sites for ALS or spinal cord injury can include the spinal cord.

Epilepsy is not truly a single disease but rather is a symptom produced by an underlying abnormality. One skilled in the art will appreciate that each epileptic subject will have damage or epileptic foci which are unique for the individual. Such foci can be localized using a combination of diagnostic methods well-known in the art, including electroencephalography, computerized axial tomography and magnetic resonance imaging. A patient suffering from epilepsy can be treated according to the present invention by implanting the GABA-producing cells into the affected site. Thus, graft sites for epilepsy include any region where seizure activity occurs. Since blockers of glutamate receptors and NMDA receptors in the brain have been used to control experimental epilepsy, cells producing molecules that block excitatory amino acid pathways may be used according to the invention. Thus implantation of cells which have been modified as described herein to produce polyamines, such as spermidine, in larger than normal quantities may be useful for treating epilepsy.

The methods of the present invention are intended for use with any mammal which may experience the beneficial effects of the methods of the invention. Foremost among such mammals are humans, although the invention is not intended to be so limited, and is also applicable to veterinary uses. The present methods can also be used in a prophylactic, palliative, and/or curative intervention in a disease or disorder process in those identified as having a disease or disorder as well as those that are suspected of having or susceptible to a specific disease or disorder.

The present invention also provides kits for carrying out the methods described herein. In one embodiment, the kit is made up of instructions for carrying out any of the methods described herein. The instructions can be provided in any intelligible form through a tangible medium, such as printed on paper, computer readable media, or the like. The present kits can also comprise one or more reagents, buffers, media, growth factors, EPO or analogs thereof, cells, molecular weight markers, enzymes, solid supports, databases, surgical equipment, computer programs and/or disposable lab equipment, such as multi-well plates, in order to readily facilitate implementation of the present methods. The kit components can be packaged in the same or separate containers as desired. Examples of preferred kit components can be found in the description above and in the following examples.

This invention is further illustrated by the following non-limiting examples.

EXAMPLES

This Example compares the functionality between grafts of freshly suspended ventral mesencephalic cells pretreated for 30 minutes with 20 IU/ml erythropoietin (EPO, N=10) or with mesencephalic cells pretreated with vehicle only (Control, N=11). Effects of the two different pretreatments were assessed by examination of rotational asymmetry after amphetamine challenge. The average number of net ipsilateral rotations per minute were recorded over a 85 minute interval. Values represent the mean±SEM for each group at 2 weeks following 6-OHDA lesion (Baseline) and 2 (2 wks), 4 (4 wks) and 6 weeks (6 wks) following administration. Significant differences between groups at each post-administration timepoint were found and are denoted by a single asterisk (*, $p<0.05$). The results of this experiment are shown in FIG. 2. As can be seen in FIG. 2, EPO pretreated mesencephalic cell suspension grafts elicited significant improvements in rotational asymmetry compared to control grafts at all time points examined ($p<0.05$).

FIG. 3 shows a comparison in survival rates of grafted tyrosine hydroxylase immunoreactive (THir) neurons between grafts treated with EPO prior to administration (EPO, N=11) mesencephalic cells and control non-pretreated (Control, N=10) mesencephalic cells. At 8 weeks post-administration grafts of EPO-pretreated mesencephalic cell suspensions administered to the denervated striatum of young adult rats possessed more than twice the number of THir neurons as control grafts. Significant differences between groups are denoted by a single asterisk (*, $p<0.05$).

FIG. 4 show low power views of freshly suspended mesencephalic cell suspension grafts pretreated with either control vehicle (Control) or erythropoietin (EPO). A coronal section illustrates a control mesencephalic cell suspension graft containing an estimated 672 tyrosine hydroxylase immunoreactive (THir) neurons and an EPO-treated graft possessing an estimated 1722 THir neurons.

The present methods can be carried out by performing any of the steps described herein, either alone or in various combinations. Additionally, one skilled in the art will realize that the present invention also encompasses variations of the present methods that specifically exclude one or more of the steps described above. As used herein "a" or "an" means one or one or more.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than" "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group or genus, but also the main group or genus absent one or more of the group members or species. The present invention also envisages the explicit exclusion of one or more of any of the group members or species from the main group or genus in the claimed invention.

All references disclosed herein are specifically incorporated herein by reference thereto.

While preferred embodiments have been illustrated and described, it should be understood that changes and modifications can be made therein in accordance with ordinary skill in the art without departing from the invention in its broader aspects as defined in the following claims.

What is claimed is:

1. A method of treating Parkinsonism comprising:
   (a) contacting a tissue graft comprising differentiated dopamine producing neurons with an effective amount of exogenous erythropoietin (EPO) or an isoform or peptide analog of EPO or administering the EPO, an isoform or peptide analog of EPO or combinations thereof to the tissue graft; and
   (b) administering the tissue graft into a compatible recipient neuronal tissue in a subject suffering from Parkinsonism, wherein the survival of cells in the tissue graft is increased, compared to cells in a tissue graft not contacted with EPO or an isoform or peptide analog thereof, wherein step (a) occurs prior to step (b).

2. The method of claim 1 wherein the effective amount of EPO or the analog thereof is from about 10 IU/mL to about 500 IU/mL.

3. The method of claim 1 wherein the compatible recipient neuronal tissue is brain tissue.

4. The method of claim 1 wherein the EPO or the analog thereof is recombinant human EPO.

5. The method of claim 1 wherein the dopamine producing neurons of the tissue graft are embryonic mesencephalic cells or are obtained from stem cells, neural stem cells, or neural progenitor cells.

* * * * *